United States Patent
Gur et al.

(10) Patent No.: US 8,216,140 B2
(45) Date of Patent: Jul. 10, 2012

(54) TONOMETER

(76) Inventors: Joshua Gur, Mishmar Hagvul (IL); Ezra Haim-Choumla, Kadima (IL); David Barash, Tel Aviv (IL)

( * ) Notice: Subject to any disclaimer, the term of this patent is extended or adjusted under 35 U.S.C. 154(b) by 1122 days.

(21) Appl. No.: 10/595,493

(22) PCT Filed: Oct. 24, 2004

(86) PCT No.: PCT/IL2004/000965
§ 371 (c)(1),
(2), (4) Date: Aug. 17, 2009

(87) PCT Pub. No.: WO2005/039379
PCT Pub. Date: May 6, 2005

(65) Prior Publication Data
US 2011/0060208 A1  Mar. 10, 2011

Related U.S. Application Data

(60) Provisional application No. 60/513,696, filed on Oct. 24, 2003.

(51) Int. Cl.
*A61B 3/16* (2006.01)
(52) U.S. Cl. .................................. 600/401; 600/561
(58) Field of Classification Search .......... 600/389–406, 600/561
See application file for complete search history.

(56) References Cited

U.S. PATENT DOCUMENTS

| | | | |
|---|---|---|---|
| 3,585,849 A * | 6/1971 | Grolman | 600/401 |
| 5,727,551 A | 3/1998 | Takagi | |
| 5,865,742 A * | 2/1999 | Massie | 600/405 |
| 6,110,110 A | 8/2000 | Dublin, Jr. et al. | |
| 6,423,001 B1 * | 7/2002 | Abreu | 600/405 |
| 6,447,449 B1 * | 9/2002 | Fleischman et al. | 600/405 |
| 6,706,001 B2 * | 3/2004 | Fresco | 600/585 |
| 7,559,898 B2 * | 7/2009 | Eide | 600/485 |
| 2002/0173712 A1 * | 11/2002 | Feldon et al. | 600/405 |
| 2004/0186367 A1 * | 9/2004 | Fresco | 600/398 |

(Continued)

FOREIGN PATENT DOCUMENTS
DE  42 13 360 A1  10/1993
(Continued)

OTHER PUBLICATIONS

PCT Search Report dated Nov. 16, 2005 of Patent Application No. PCT/IL2004/000965 filed Oct. 24, 2004.

(Continued)

*Primary Examiner* — Max Hindenburg
*Assistant Examiner* — Michael C Stout
(74) *Attorney, Agent, or Firm* — Maine Cernota & Rardin

(57) ABSTRACT

A self-operated non-contact tonometer for measuring the intra-ocular pressure of an eye, projecting light into the eye and measuring the reflected light as affected by mechanical distortion. The cornea is distorted by delivering a pneumatic pulse. The tonometer consists mainly of an electro-optical unit mountable on the head of a user and a control unit. The control unit of the tonometer includes a display and optionally an audio device for instructing the user. The electro-optical unit employs a tubular wave guide, a light detector, and a reflector for deflecting a light beam to the eye and for eliminating a part of the reflected light reaching the detector. The aligning of the tonometer with the head of the user is optionally assisted by a reticle.

8 Claims, 4 Drawing Sheets

U.S. PATENT DOCUMENTS

2004/0236204 A1 * 11/2004 Feldon et al. ................. 600/406
2005/0020896 A1 * 1/2005 Fuller et al. ................... 600/405

FOREIGN PATENT DOCUMENTS

EP  0267022 A  5/1988
EP  315329 A2 *  5/1989
JP  2003 299622 A  10/2003

OTHER PUBLICATIONS

EP Search Report dated Mar. 2, 2009 of Patent Application No. 04770628 filed Oct. 24, 2004.

* cited by examiner

TONOMETER

CROSS REFERENCE TO RELATED APPLICATIONS application Ser. No. 10/595,493 is a nation stage entry of PCT/IL04/00965 filed on Oct. 24, 2004 which claims priority to U.S. Provisional application No. 60/513,696 filed on Oct. 24, 2003.

TECHNICAL FIELD OF THE INVENTION

The present invention relates generally to tonometry and more particularly to non-contact tonometry. The invention also relates to measurement of intra ocular pressure (IOP) and to devices for measuring the same.

BACKGROUND OF THE INVENTION

The significance of measurement of the hydrostatic intra-ocular pressure (IOP) is well known in medicine (ophthalmology). Excessive internal eye pressure is a cause of glaucoma and other eye diseases.

Professional medical staff, using a variety of methods—mainly the indentation tonometry, the applanation tonometry and the non-contact tonometry, perform common measurements of IOP. Several systems are available in the market. An indentation tonometry system is the Schiotz tonometer, which dates back to the nineteen thirties. A more recently developed system is the Mentor Tono-Pen XL from Mentor O&O, Inc. of Norwell, Ma US. An applanation tonometry system is the Goldman tonometer, which is a standard tonometer in a considerable amount of medical institutions. The above mentioned systems and methods are based on direct contact with the corneal eye associated with liquids and medications applied to the eye. A non-contact tonometry is preferable since it decreases hazards to the tested eye associated with the measurement process. A non-contact tonometry system is the puff tonometer XPERT NCT from Reichert Cambridge US. Puff tonometry employs detecting changes in the reflectance of a cornea, which is distorted by a pneumatic pulse. The measurement process basically includes the steps of: (i) placing and aligning the tonometer in front of the tested eye; (ii) measuring the intensity of a light reflected by a test area within the surface of the cornea; (iii) distorting the cornea by projecting a pneumatic pulse towards it, and (iv) matching features of the intensity-time profile of the light reflected by the distorted cornea with IOP values. The accuracy of IOP values obtained is considerably affected by misplacement or misalignment of the tonometer. Therefore allowed tolerances of placement and alignment are significantly narrow.

Once a patient is diagnosed as suffering from excessive eye pressure, he/she is to have IOP monitored periodically—typically at different hours during the day. It is desirable that a user is be able to measure his or her own IOP at home, rather than make special visit to the clinic for this purpose. However, current commercially available devices providing for self—examination of IOP are not satisfactory mainly due to accuracy and cost considerations.

Therefore, efforts to develop a self-operated tonometer suitable for home medicine are ongoing. U.S. Pat. No. 6,440,070 discloses a device consisting of a gauge, which is pushed against the eyelid while force is measured. An ultrasound-measuring device is also used to measure a distance from an internal object within the tested eye. Correlating the force applied to the displacement of the pressed surface caused by this applied force provides assessment of pressure. U.S. Pat. No. 6,746,400 discloses a system implementing of a plurality of pressure sensors providing also a spatial distribution of pressure from which IOP can be derived. Both above mentioned inventions involve direct or indirect contact with the tested eye. Measured IOP values obtained thus are considerably less sensitive to fitting or aligning of the measuring gear as compared to those obtained by current systems employing optical measurements. However, patients tend to decline using a measuring system which entails applying force by touching the eye.

DETAILED DESCRIPTION OF THE PRESENT INVENTION

The present invention provides a method for determining internal pressure within deformable bodies by measuring the dynamics of reflectance changes from the body in response to mechanical disturbance applied to the body. The method provides considerably wider tolerances in placement and alignment of the tonometer related to the test area without sacrificing essential measurement accuracies. The method is suitable for measuring internal pressure within most kinds of deformable bodies having a convex surface and in particular for measuring intra ocular pressure (IOP).

Figure 1:
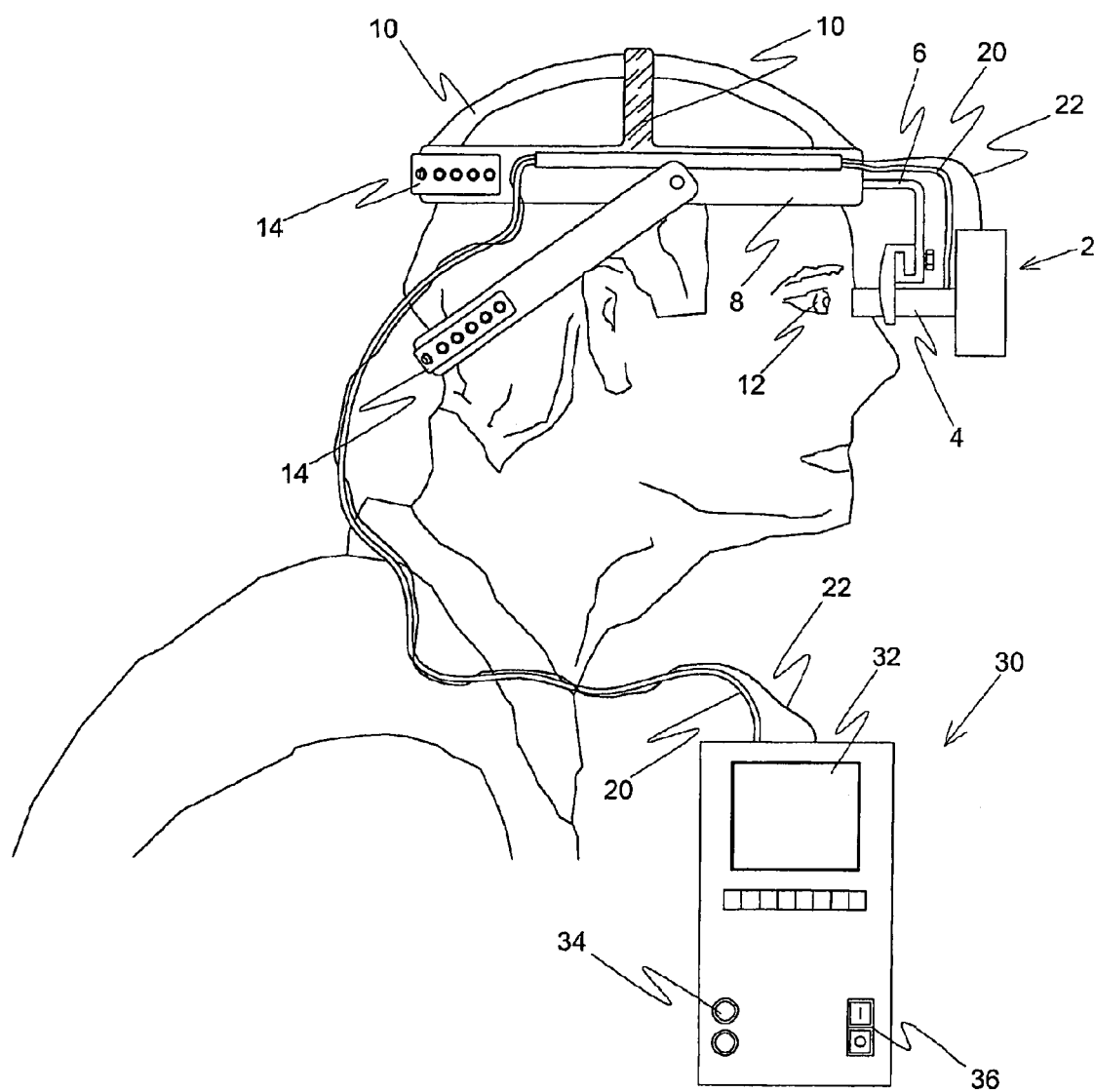
FIG. 1 is schematic side view of a non-contact tonometer as applied to patient according to a preferred embodiment of the present invention.

Reference is made to FIG. 1 showing a tonometer adapted for measurement of IOP, according to a preferred embodiment of the present invention. Electro-optical unit 2 having a cylindrical extension 4 is placed in front of a patient. The electro-optical unit is attached by means of a connecting device 6 to a mounting device consisting of frame 8, which is placed over the patient's head. Strips 10 supporting frame 8 over the head, and the aperture which faces eye 12 (not shown) is fixed in place by means of adjustable strips 14 by urging the frame against the patient's forehead. The mounting device of this tonometer consists of frame 8, strips 10, strips 14 and connecting device 6. Connecting device 6 is slidably attached to frame 8 in front of either left or right eye by means of a clamping device or screw (not shown). A flexible tube 20 conveying compressed air and a power and signal cable 22 connects electro-optical unit 2 with control unit 30 of the tonometer. A display 32 on which operating instructions and measurements results are shown, is located at the front panel of control unit 30. Functional keys 34 and main operating switch 36 are also installed on this front panel. The user (patient) initiates the operation by attaching the electro-optical unit 2 to frame 8 in its pre-assigned place for attending to the left or right eye. After turning operating switch 36 on, the user mounts frame 8 over the head and adjusts its placement by means of the adjustable strips 14 to fit in front of the selected eye. By turning the system on, an illuminating beam is emitted from an optical aperture located on the side of the electro-optic unit facing the user. By pressing a functional key the user hears a sound changing its pitch and/or watches the display, on which intensity of reflected light from the surface of the eye is shown, to maximize the intensity and improve placement and pointing of the electro-optical unit in front of the eye. The patient can also activate a reticle by pressing another functional key and center it in his field of view, by which the test area is centered over the corneal apex. The frame which is adjusted to the user forehead by means of adjustable supporting strips, secures the position and keeping the user-devise combination stable.

Different mounting configurations are possible, as long as the electro-optical unit remains stably mounted on the patient. Another preferred embodiment of a self-operated tonometer according to the present invention takes the form of goggles attached to the user's head by means of flexible strap. In such a case, the electro-optical unit is attached to the goggles corresponding to the selected eye by means of clamping connectors.

Figure 2:
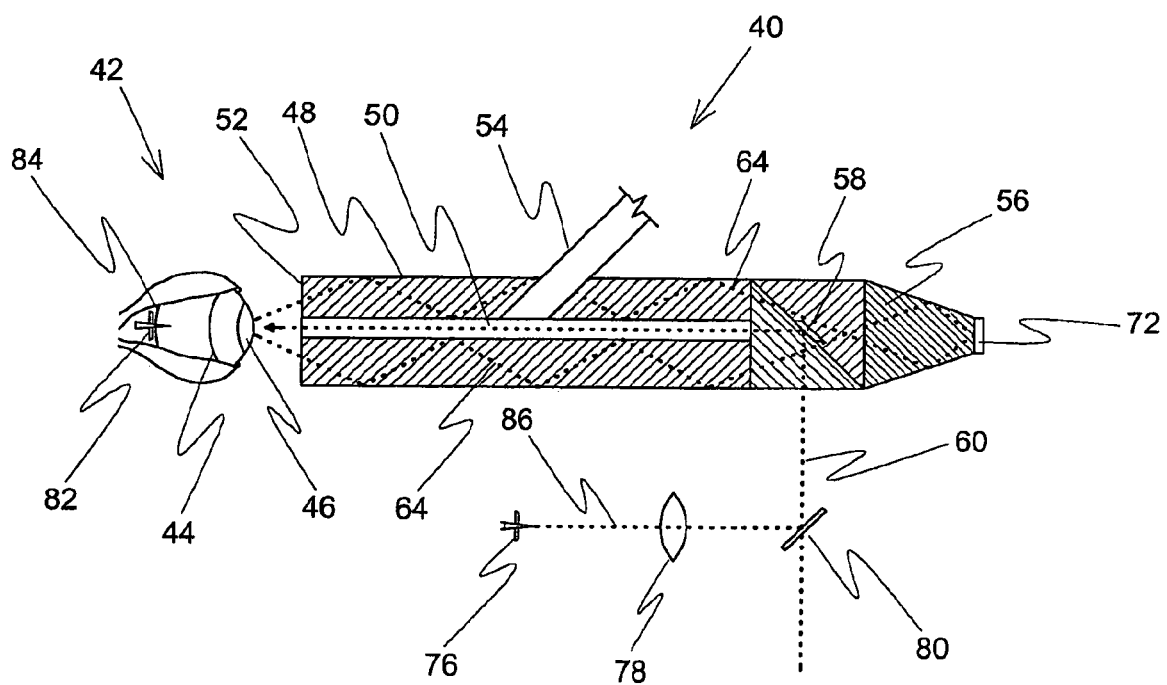
FIG. 2 is a schematic longitudinal sectional view of a segment of the optical unit of the non-contact tonometer of the invention.

Reference is now made to FIG. 2, showing a schematic longitudinal sectional view of a segment 40 of the electro-optical unit 2 of a tonometer of the invention. Segment 40 of the electro-optical unit 2 is placed in front of a user's eye 42. IOP is typically measured in the area of the cornea 44, preferably at its center, (which is the location of the pupil). Therefore the electro-optical unit 2 is pointed toward the cornea 44 on which a substantially central sector 46 is to be illuminated. In a preferred embodiment of the invention, there is provided a unitary device which includes both a light projecting element and a collecting tube (LPCT). The LPCT 48 is positioned in front of the pupil taking care not to touch the eyelashes. LPCT 48 has a substantially thick wall defining a narrow lumen 50 (constituting an internal bore). The proximal face 52 of LPCT 48 is coated with a suitable anti-reflecting coating. A flexible tube 54 is provided with its proximal end coupled to a side surface of the lumen 50 and is connected at its distal end to a source of compressed air (not shown). The light guide 56 is attached to the distal face of LPCT 48 by means of a refraction index-matching glue or any suitable glue such as EPOTEC® (a commonly used optical glue). The distal face 52 of the light guide 56 conforms to the proximal face of LPCT 48. The light guide 56 assumes the shape of a frustum of a pyramid or a cone towards its distal end. A light reflector 58 consisting of a highly reflective, diagonally mounted plate, is attached to the inner surface of the light-guide 56. This reflector 58 deflects an illuminating beam 60 directing it along the axis of LPCT 48 to the central sector 46. The light source emits a collimated light, typically from a light emitting diode (LED) or a laser (not shown).

The list of reflected light receiving surfaces includes the coated proximal face 52 of the wall of LPCT 48, reflector 58, and light detector 72. The positioning of light reflector 58 considerably reduces the contribution of light reflected by the corneal apex to the total intensity received by the light detector 72. Therefore the electro-optical system of the invention is less sensitive to the alignment with the face of the user. The fact that the illuminating beam, the pneumatic pulse and the detector share the same axis makes the system less vulnerable to axis misalignments.

The wall of LPCT 48 provides for reflecting and delivering reflected light 64 to detector 72 and is referred to hereinafter as light collecting and delivering device. In the embodiment shown in FIG. 1 the light guide 56 constitutes a light-guiding device that serves to direct light reflected by the eye to a detector without passing axially through the lumen 50. Optionally, the LPCT 48 consists of a tube though which illuminating light is projected to the body whose internal pressure is measured, surrounded by bundles of fiber optics.

In such a case all the bundles of fiber optics are grouped together to form a densely packed bundle and the respective face of each fiber is directly attached to the face of light detector 72. Such a densely packed bundle serves to concentrate the light reflected from the patient's eye prior to its striking the detector and functions as the light guiding device constituted by the light guide 56 in the embodiment shown in FIG. 2. Furthermore, the bundles of fiber optics need not cover the entire surface of the tube densely. Any substantially tubular body whose wall is either monolithic or consists of discrete transparent longitudinal members having suitable refracting index can function as a light collecting and delivering device. Similarly one or more such transparent members or bundles of fiber optics are applicable. However, the light collecting and delivering device preferably surrounds the volume through which illuminating light is projected to the body whose internal pressure is measured.

Mounting the device on the user's head is followed by aligning the device on the user's face regulated by maximizing the intensity of reflected light received by the detector. Such a procedure is more suitable for a skilled and trained operator. In order to make the tonometer of the present invention suitable for self-examination of IOP, a reticule is used to simplify the alignment and attaching steps. The patient observes reticle 76 through lens 78 and a beam splitting device 80. When the user has reticle image 82 centered in the field of view on his/her retina 84 an actuation button is pressed triggering the measurement process. The intensity of light reflected from the cornea is measured by the detector 72, connected to the electronic subsystem (not shown). The controller unit of the system subsequently sends an instruction to an air switch (both are not shown in this drawing) to release a pulse of compressed air through the flexible tube 54 and subsequently to the tube 50. The pulse of compressed air, which is directed at sector 46 transiently deforms the cornea distorting its curvature, making it temporarily flatter or even concave. The light beam illuminates the eye where the cornea has been distorted and the changes in geometry yield correlated changes in the amount of reflected light that is captured by face 52 of LPCT 48. This reflected light is then detected by light detector 72, which translates the changes in light intensity into changes in an electric signal. This electric signal is further sampled and digitized yielding a series of digital values further sent to the central controller unit for analysis.

Figure 3:
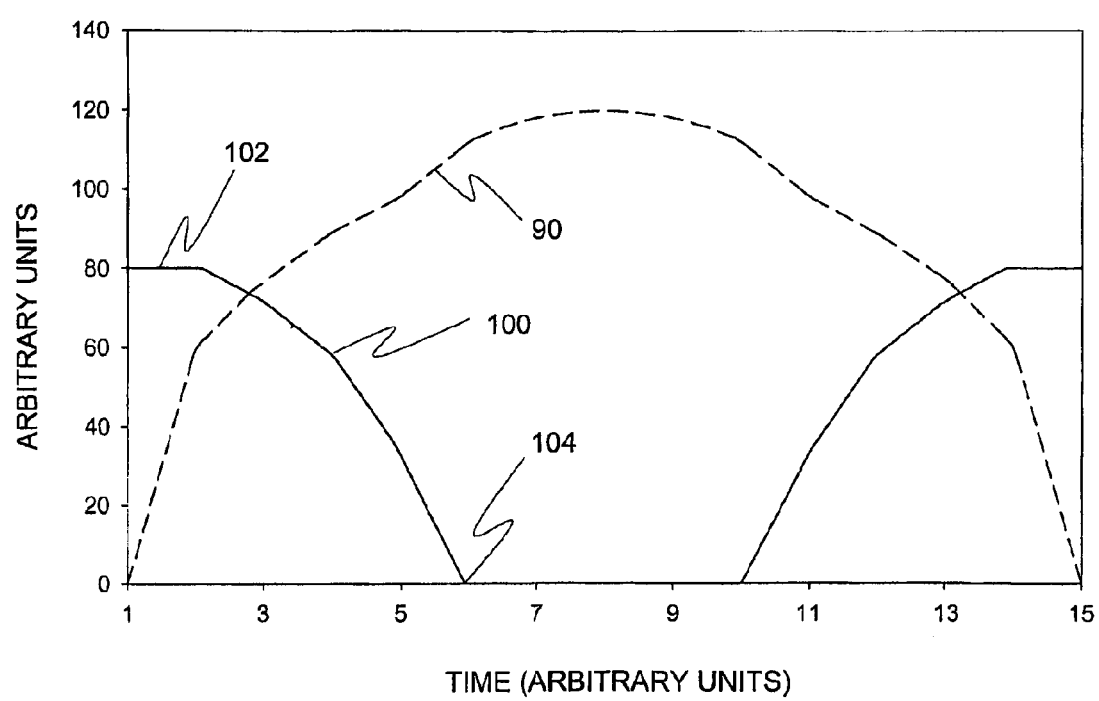
FIG. 3 is a graph describing simulated pressure of compressed air and intensity of reflected light versus time for the tonometer.

Reference is now made to FIG. 3 showing a graph of simulated pressure readings and intensity of reflected light versus time as generated by the non-contact tonometer of the invention. Pressure values of graph 90 represent measurements made inside the flexible tube near the aperture. The intensity of reflected light at the light detector face is represented by plot 100. The intensity of received reflected light is maximal as shown by segment 102, which corresponds to reflection from the undistorted cornea. The larger volume of the lumen of tube 50 of FIG. 2 and the diversion of the compressed air as it passes the aperture cause pressure values rise at the cornea surface to lag behind in time with respect to the pressure rise at the measuring point. Therefore the cornea maintains its undistorted curvature as the pressure values rise at the measuring point. Flattening of the cornea starts a while after the pneumatic pulse is initiated and similarly the eye resumes its original curvature somewhat before the pressure change is nullified. The cornea is flattened at point 104 in which the intensity is zeroed. The cornea is illuminated with a narrow beam emitted from tube 50 of FIG. 2. A convex surface of the undistorted cornea implies a larger effective area, which reflects light back towards face 52 of FIG. 2. A planar surface has smaller effective area, which reflects this illuminating light towards face 52 of LPCT 48 of FIG. 2, and therefore correlates with a lower light intensity reflected. When certain threshold low reflection intensity is reached, a zero reflectance value is assigned and any lower light intensity reflected is interpreted as zero, even as the cornea assumes a concave structure.

Features of intensity-time profile 100 are correlated with actual IOP values. IOP values are correlated with the time intervals in which light intensity changes from its maximal value to zero and back again to its maximal value. Higher IOP values correspond to shorter time intervals, at a given pressure-time profile and longer time intervals correspond to lower IOP values. Therefore measuring this time interval and comparing it with equivalent time intervals measured related to eyes with given IOP, results in an IOP value. Time interval, which is less accurate, may equal the time length of the pneumatic pulse. Alternatively, an IOP value is calculated by comparing the slope of the change in light intensity with equivalent slopes measured related to eyes having given internal pressure. The IOP value of the measured body is determined by associating such time-related features of the measured curve with a given IOP value. These time-related features associated with IOP values are pre-stored in the central controller. Therefore IOP is determined by matching time-related features of measured changes in light intensity with pre-stored IOP values.

An IOP value is displayed followed by a message indicating the user that the measurement process has proceeded properly. Fault indications are displayed when signal intensity, or pressure values exceeds its typical ranges. The user is instructed to activate a built-in self-examination procedure and repeat the measurement process if it indicates that the tonometer functions properly. Repeated process starts by checking mounting of the tonometer in front of the eye and centering the reticule image in the field of view.

Figure 4:
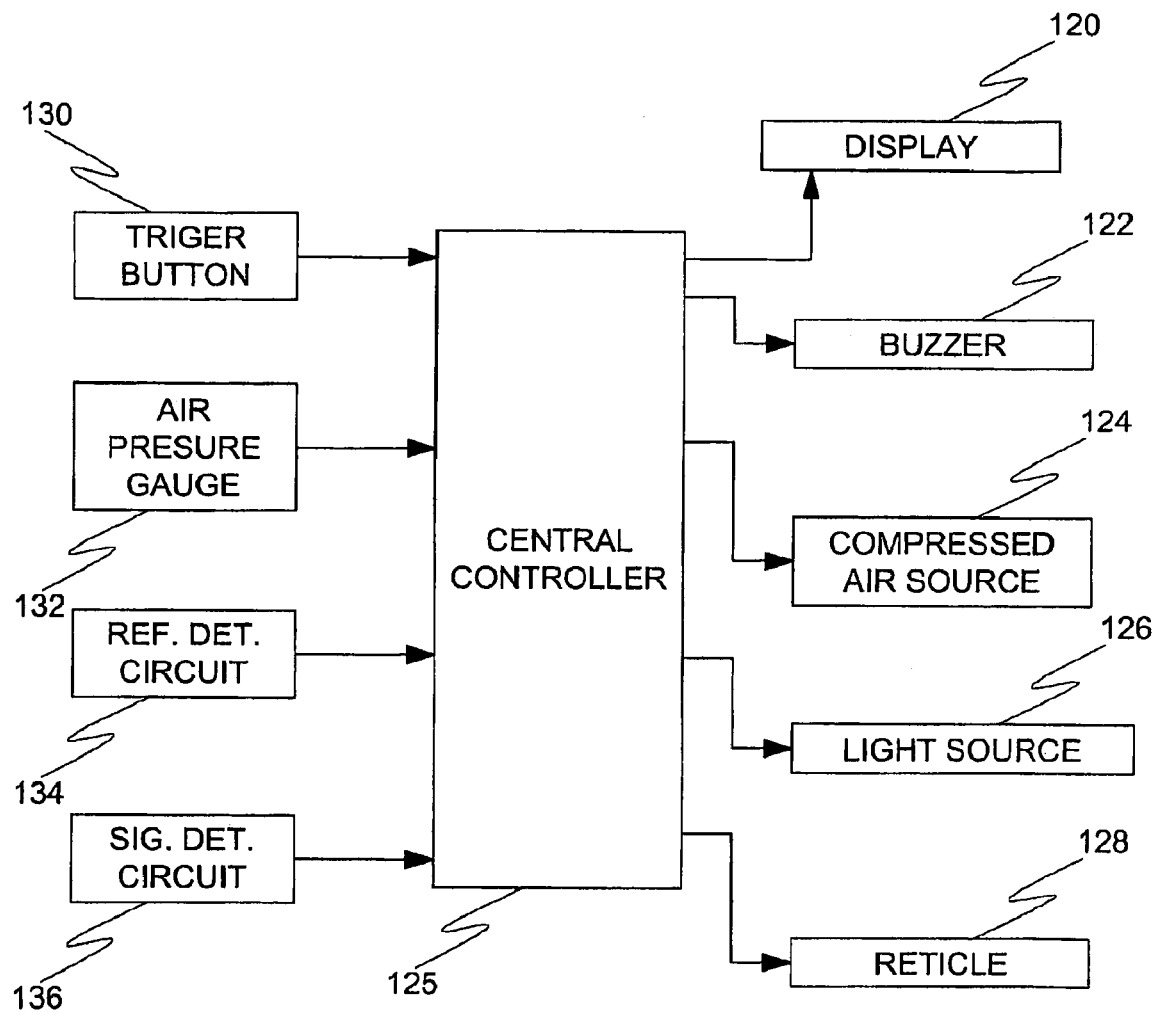
FIG. 4 is a schematic block diagram of the control unit showing main components.

Reference is now made to FIG. 4 showing a block diagram of the electronics sub system of a preferred embodiment of the present invention. Display 120 displays instructions to the user as well as results of the measurements. A suitable display device is employed for example a LED/LCD display. Buzzer 122 is a device that makes an audible sound when the attention of the user has to be called to the display. This happens if the measurement fails, or if the battery is low, etc. It also changes its pitch following the intensity of the received signal during the placement and pointing phase. Compressed air source 124 operates on a command from central controller 125, to project a pneumatic pulse into the system. The driver of illuminating light source 126 and reticule 128 are controlled by the central controller. Trigger button 130, which is also connected to the central controller initiates the measurement process when pressed by the user after placing and aligning the optical unit with the eye to be tested. Safety air pressure gauge 132 is used in the air release system, to stop the airflow if it exceeds the specified limits of flow or duration. Light detector circuitry of a reference detector 134 and of signal detector 136, include synchronized sampling and digitizing means implemented by suitable sample and hold devices and analog to digital converters, and are connected to the central controller feeding it with data. Reference detector circuit 134 processes the information from a reference detector. The signal detector circuit 136 picks up the information from the light detector not shown, triggered by the reference signal created at the reference detector circuit. This optional reference trigger arrangement enables this circuit to detect very weak signals and thus be very sensitive.

The tonometer according to this preferred embodiment is particularly suitable for self-examination carried out in the convenience of the patient's home. In a preferred embodiment of the present invention a tonometer having an electro-optic unit and a control unit, is mounted on a frame that can be placed on a table. This frame has a curved support on which the patient leans his forehead for aligning the electro-optical unit with the eye. In such an embodiment, alignment of the gear with the eye is confirmed by the medical staff, by watching the intensity level of detected reflected light.

Another variant consists of a plurality of electro-optical units, all linked to one central control unit consisting of PC. The electro-optical units are mounted on a frame that allows several different patients to be examined and their IOP determined.

The invention claimed is:

1. A method for measuring internal pressure of a body comprising:
   aligning with the body a longitudinal axis of a light collecting and delivering device having a wall and an axially extending lumen;
   illuminating the body by way of the light collecting and delivering device and applying thereto a pneumatic pulse capable of substantially flattening the body, the illuminating light beam and the pneumatic pulse passing axially through the lumen,
   guiding by total internal reflection through the wall of the light collecting and delivering device light reflected from the body to a detector when the body is in a non-flattened configuration, at least a portion of the light when the body is in a flattened configuration being reflected into the lumen and prevented from reaching the detector; and
   matching a time-related feature associated with said changes in the light intensity of light reflected to the detector with a given pressure value related to mechanical disturbance,
   wherein said time related-feature is at least one of: a time length of said pneumatic pulse, a time interval in which said changes of said light intensity measured are detected, and a slope of said changes of said light intensity measured.

2. The method for measuring internal pressure of a body as in claim 1, wherein said time-related feature is a slope of said changes of said light intensity measured.

3. The method for measuring internal pressure of a body as in claim 1, wherein said body is an eye and the aligning comprises centering a reticule image in a field of view of the eye.

4. The method for measuring internal pressure of a body as in claim 1, wherein said light collecting and delivering device is a unitary light projecting and collecting device tube (LPCT).

5. A device for measuring internal pressure of a deformable body, said device comprising:
   a light collecting and delivering device formed of a wall surrounding a lumen, the wall having an end surface for receiving light reflected by the body, the light being guided to travel along the wall by total internal reflection within the wall,
   an illuminating beam source for providing a light beam to the body, the light beam passing through the lumen of the light collecting and delivering device;
   an air source for providing a pneumatic pulse of compressed air to the body by way of the lumen of the light collecting and delivering device to flatten a convex surface of the body;

a light detector mounted to receive light reflected by the body and passing through the wall of the light collecting and delivering device when the body is in a non-flattened configuration; and a control unit connected to the detector to provide a measure of the internal pressure of the body.

6. The device as in claim 5, wherein said deformable body is an eye and the device further comprises a reticule for projecting an image thereof on the eye.

7. The device as in claim 5, further comprising a mounting for securing to a head of a user.

8. The device as in claim 5, wherein:

the control unit is adapted to match a time-related feature associated with changes in the light intensity of light reflected to the detector with a given pressure value related to mechanical disturbance; and the time related-feature is at least one of: a time length of said pneumatic pulse, a time interval in which said changes of said light intensity measured are detected, and a slope of said changes of said light intensity measured.

* * * * *